US006287576B1

(12) United States Patent
Bgatov et al.

(10) Patent No.: US 6,287,576 B1
(45) Date of Patent: *Sep. 11, 2001

(54) BIOSTIMULATING AGENT

(75) Inventors: Vasily Ivanovich Bgatov; Evgeny Mikhailovich Blagitko; Natalya Georgievna Mezentseva; Tatyana Ivanovna Novoselova; Boris Yakovlevich Novoselov; Alexei Ivanovich Surnin, all of Novosibirsk (RU)

(73) Assignee: Zakrytoe Aktsionernoe Obschestvo Nauchno-Proizvodstvennaya Firma "NOV", Novosibirsk (RU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/027,905

(22) Filed: Feb. 23, 1998

(30) Foreign Application Priority Data

Nov. 17, 1997 (RU) ................................................. 97118466

(51) Int. Cl.[7] ....................................................... A61K 9/00
(52) U.S. Cl. .......................... 424/400; 424/464; 424/489
(58) Field of Search ..................................... 424/489, 464, 424/400

(56) References Cited

U.S. PATENT DOCUMENTS

| 4,551,331 | 11/1985 | Rudin | 424/195.1 |
|---|---|---|---|
| 5,140,949 | 8/1992 | Chu et al. | 119/174 |

FOREIGN PATENT DOCUMENTS

| 2 717 692 | 3/1994 | (FR) . |
|---|---|---|
| 2016574 | 7/1994 | (RU) . |
| 2040269 | 7/1995 | (RU) . |
| 2063229 | 7/1996 | (RU) . |
| 2082403 | 6/1997 | (RU) . |

OTHER PUBLICATIONS

Kimura et al., Effects of soluble sodium alginate on cholesterol excretion and glucose tolerance in rats, J. Ethnopharmacol. 54(1);47–54, 1996.

Berg et al., Experimental and clinical studies on the effect of natural substances on the crystallization of calcium oxalate, Fortschr. Urol. Nephrol., 17(8);391–403, 1981.

Golyshenkov et al., Effectiveness of birch fungus (extract) and neomycin in calf dyspepsia, Veterinariya 5;91, 1977.

Primary Examiner—Thurman K. Page
Assistant Examiner—Todd D Ware
(74) Attorney, Agent, or Firm—Blank Rome Comisky & McCauley LLP

(57) ABSTRACT

The present invention relates to a biostimulatinq agent comprising natural minerals having ion-exchanges and sorption properties, and also a biologically active vegetable stock, the natural minerals including a clinoptylolite-heulandite zeolite containing not less than 92 wt % of clinoptylolite, and/or montmorillonite clay containing not less than 92 wt % of montmorillonite, and as the biologically active vegetable stock comprises wheat bran, rye bran, oats, Japanese laminaria, madder, birch fungus, and the like.

The biostimulating agent of the present invention normalizes the mineral balance of the body, produces higher therapeutical effect, for example, in using it in case of intestinal tract diseases, aterosclerosis, urinary calculosis, produces an immune-modulating and tonic effect.

13 Claims, No Drawings

BIOSTIMULATING AGENT

BACKGROUND OF THE INVENTION

The present invention relates to drugs, more particularly to a biostimulating agent comprising natural minerals having ion-exchange and sorption properties, and biologically active vegetable stock. At present, it is well known to use as drugs natural minerals having sorption and ion-exchange properties. Natural zeolite with tuff-containing clinoptilolite 68–88 wt % used in particular as an antiallergic agent and as an agent for removing radionuclides accumulated in the body (see RF Patent No. 2063929, class A61K 33/00 and RF Patent No. 2082436, class A61K 33/00).

It is also well known to use a natural zeolite based biostimulating agent which further comprises an extract composed of verdant oak branches (RF Patent No. 2040269, A61K 35/78).

Well known in the art is also clay based drug which is characterized in that natural mineral illite constitutes at least 50% in said drug (French Patent No. 2717692, A61K 33/06). The drug is useful for external and internal administration in case of infectious diseases such as otitis, rheumatism, cystitis and also in case of gastric diseases. Besides, the drug is recommended as a general health improving.

It is well known to use natural mineral such as montmorillonite or clinoptilolite as enterosorbents for withdrawing toxic and pathogenic components from the body of warm-blooded animals and humans(RF Patent No. 2016576, A61K 33/00). To perform such administration, natural minerals are preliminary purified. The resulting mineral stock is introduced into the intestine. The optimum amount of a daily dose of the natural mineral ranges from 0.1 to 1.0 g per kg of the body weight.

The effect of all the drugs mentioned above is based on ion exchange and sorption properties of zeolite containing tuffs and montmorillonites. However, the known drugs do not permit using all possibilities of the abovementioned natural minerals which have a wide spectrum of macro-and microelements to a full degree.

SUMMARY AND OBJECTS OF THE INVENTION

The object of the invention is to provide biostimulating agents based on using both natural minerals having ion exchange and sorption properties and biologically active vegetable stock.

The biostimulating agent according to the invention is characterized in that that it comprises, as natural minerals, clinoptilolite-heulandite zeolite containing not less than 92 wt % clinoptilolite and/or not less than 92 wt % montmorillonite in montmorillonite clay, and biologically active vegetable stock, e.g., cereals such as oats or waste thereof, such as wheat and rye bran; sea algae such as Japanese laminaria (*Laminaria japonica Aresh*); higher plants such as madder (root) (*Rubia tinctorum*) higher fungi such as birch fungus (*Ionotus obliquus*).

The essence of the invention is to use to the fullest measure the properties of natural minerals as suppliers of macro-and microelements to the human organism, sorbents and ion exchangers capable of restoring normal mineral composition of the organism and thus promoting normalization of all metabolic processes. This is achieved by using a maximum of pure mineral stock containing not less than 92 wt % clinoptilolite and/or montmorillonite. Surprisingly it was found that a combination of zeolite and/or montmorillonite of such quality with biologically active vegetable stock makes it possible to maintain effectively the desired mineral salt balance in the body. When in the digestive tract, natural minerals are subjected to exchange reactions with digestion products. In this case, on the one hand, minerals become crushed, their active surface becomes large, and on the other hand, there occurs ion exchange in the "mineral-body" system. Micro-and macroelements present in the minerals diffuse into the body, whereas free mineral bonds are substituted by the elements which are present in the body in excessive amounts.

Use of various compositions based on the abovementioned minerals and biologically active vegetable stock intensifies specific properties of this vegetable stock. Useful compounds which are present in the vegetable stock become the most effective in the human body, provided there is a certain ratio of micro and macroelements essential both for entering these substances into the body from the intestine which process never takes place due to absence of micro- and macroelements and for allowing the entry of substances present in the vegetable stock into the metabolic processes in the body.

DESCRIPTION OF THE INVENTION

As disclosed in the invention, the biostimulating agents comprising up to 92 wt % of purified clinoptilolite and/or montmorillonite in combination with biologically active vegetable stock are, on an average, by 60–70% more effective than drugs containing individually mineral stock or individually biologically active vegetable stock. Such high effectiveness of the claimed agents results from a synergist effect of combination of mineral and vegetable stock that intensifies the activity of each other. In addition, the indirect effect of the mineral stock on the homeostasis regulation mechanism becomes stronger due to the fact that the body is capable of using most effectively the therapeutic potential of the biologically active vegetable stock. The biologically active vegetable stock accelerates, assisted by the active substances present therein, the processes of a positive effect of the mineral stock on the human body.

In order to prepare the biostimulating agent of the invention, natural minerals (e.g. Kholin deposit of zeolite-containing rocks) i.e. zeolites comprising clinoptilolite and heulandite and montmorillonite clay previously purified to not less than 92 wt % of clinoptilolite and its geochemical varieties or monotmorillonite are used.

In order to prepare the biostimulating agent of the present invention, biologically active, preferably dry vegetable stock, e.g. wheat and rye bran, oats, Japanese laminaria (Liminaria japonica Aresh) madder root (Rubia tinctorum), birch fungus (Ionotus obliquus) is used.

Bran is flour grinding production waste resulting from milling the grains. Bran comprises various particles of grain envelopes in admixture with flour and germs. Bran is the main supplier of cellulose which is a vitally important substrate without which the digestive tract and all the other systems in the human body cannot function properly. Cellulose, which is a main integral part of the vegetable cell envelope represents carbohydrate from the group of polysaccharides composed of glucose in molecule remnants. The main property of cellulose is its ability to adsorption. While in the intestine of the human body, cellulose starts imbibing a liquid thus binding simultaneously excessive amount of gastric juice enzymes and hydrochloric acid. Bran, while being a supplier of cellulose promotes optimization of enzymatic activity and reduces aggressiveness of the gastric juice. Bran, while acting indirectly through a pressure normalization mechanism in the bile duct and also normalizing peristatis of the duodenam and eliminatins congestion of a food clot, makes it possible to considerably alleviate the course of diseases such as cholecystitis and dyskinesia of the bileferous tracts.

From among cereals, oats is used. Oats is a cereal rich in protein, amino acids, vitamins, sugars, and fatty acids. Oats is one of the main sources of vegetable fats which are structural cell components.

In medical practice oats is used as a general health improving agent, and in case of intoxications as a diuretic cholagoque, sudorfic and enveloping agent. Oats is an agent which produces a pronounced positive effect in case of inflammatory diseases of the intestinal tract (chronic cholecystitis, gastritis duodenitis, enteritis or the like). Besides, polyphenols present in oats promote reducing cholesterol and low-density lipoproteides causing development of atherosclerosis.

Japanese Laminaira (*Laminaria japonica Aresh*) is a valuable supplier of organic iodine compounds which improve assimilation of protein, phosphorus, calcium and iron, reduce the viscosity of blood, lower the tension of blood vessels and arterial pressure. Japanese laminaria also promotes lowering of cholesterol in blood plasma and inhibits development of atherosclerosis and produces a regulating effect on the functioning of the thyroid gland and ovaries. Madder (*Rubia tinctorum*) is a herb capable of destroying and loosening kidney and vesical calculi, and also produces a spasmolytic and diuretic effect, promotes migration of calculi and withdrawal thereof from the kidneys and urinary tracts. The plant roots are preferably used. They are useful in case of urolithiasis-pyelitis and inflammation of the urinary bladder.

Birch fungus (*Ionotus obliquus*) is a higher fungus from the class of Basidial fungi and it is useful in case of chronic gastritis, dyskinesia of the gastro intestinal tract aggravated by atonia, gastro ulcer and duodenal, peptic ulcer.

Birch fungus is prescribed also as an additional symptomatic agent which improves the general state of oncological patients, predominantly in case on malignant neoplasms in the stomach and the intestine. Birch fungus also produces good general tonic and analgetic effect, this being.

This is undoubtedly useful not only in case of oncological diseases but also in other situations, e.g. in case of a chronic fatique syndrom. Birch fungus is extremely rich in biologically active substances such as organic acids, polysaccharides, resins, macro- and microelements and other substances. These factors widen the entire spectrum of medicinal properties of this agent.

The claimed biostimulating agent can be prepared as follows. Mineral and vegetable stock comprising clinoptilolite nevlandite zeolites containing 92 wt % clinoptilolite, wheat bran, rye bran and water are used, the ratio of the components being as follows (wt %):

50 zeolite; 25 wheat bran; 20 rye bran; and water to the balance.

The whole stock is crushed or ground, e.g. zeolites are crushed to particle size of not greater than 0,1 mm, e.g. 0.05 mm. Bran and zeolites are then examined visually for foreign inclusions and sifted through a screen using generally known techniques. Besides, a permanent magnet is used for treating magnetically the components to remove some foreign inclusions. After this operation, each of the components is calcined in temperature-controlled for drying cabnets 30–60 minutes to be dehydrated, cleaned from gases and decontaminated, zeolites are calcined at 200–300° C. and bran at 130–50° C. After calcination, the components are metered in amounts specified for the formulation and mixed in a special mixer to form a homogeneous compound, one kg of the mixture comprises 500 g of zeolites, 250 g of wheat bran, 200 g of rye bran and 50 g of water to obtain a homogeneous powder.

Prior to subsequent packing the biostimulating a powder-like agent is additionally sterilized at 120° C. for 30 minutes.

The biostimulating agent according to the invention can be any standard drug, e.g. powder, granules, tablets, lozenges, pills or the like.

The biostimulating agent in the form of tablets is prepared as follows. A certain amount of cellulose is added to the resulting dry homogeneous compound of a powder-like agent, the mixture is maintained while periodically stirring for 12–24 hours till natural moisture saturation is achieved. The compound is then pressed using standard equipment at 130–150° C., a pressure of 60–80 MPa for 1 minute to obtain tablets with a weight from 0.5 to 5 g.

Examples given below serve to describe the present invention in greater detail.

1. Biostimulating agent No. 1 in the form of granules comprises (wt %):

| | |
|---|---|
| zeolite | 50 |
| wheat bran | 25 |
| rye bran | 20 |
| water | 5 |

2. Biostimulating agent No. 2 in the form of tablets comprises (g):

| | |
|---|---|
| montmorillonite | 0.5 |
| Japanese laminaria | 0.45g |
| water | 0.05g |
| | 1.0 |

3. Biostimulating agent No. 3 in the form of granules comprises (wt %)

| | |
|---|---|
| zeolite | 30 |
| montmorillonite | 30 |
| oats | 35 |
| water | 5 |

4. Biostimulating agent No. 4 in the form of granules comprise (wt %)

| | |
|---|---|
| zeolite | 15 |
| montmorillonite | 20 |
| madder root | 60 |
| water | 5 |

5. Biostimulating agent No. 5 in the form of granules comprises (wt %):

| | |
|---|---|
| zeolite | 15 |
| montmorillonite | 20 |
| birch fungus | 60 |
| water | 5 |

Clinical Tests

EXAMPLE I

Biostimulating Agent No. 2

The drug is taken in the form of tablets, 2 or 3 tablets 3 times a day, the weight of a tablet is 1 g.

The drug was tried on 40 volunteers (20 woman and 20 men aged from 42 to 64). The drug in-take course lasted 45 days, and the following results, were achieved.

1. 80% of patients exhibited a reduced cholesterol content by 9–13% . Prior to the administration course, the cholesterol content was 7.2–7.8% and after the administration course the cholesterol content was 5.9–6.7%.

2. 76% of patients who had excessive body weight, experienced a 10–15% reduction of the weight. The initial body weight was 96–112 kg, and after the drug intake course, the body weight decreased to 84–98 kg.

3. 80% of patients who suffered from constipations had fewer constipations.

4. 72% of patients who took the drug of the present invention showed increased number of T and B -lymphocytes by 12–16%.

5. 92% of patients who took the drug of the present invention showed greater working capacity and reduced fatique.

6. 88% women who had preclimacteric and climacteric neurosis showed higher spirits and less tearfulness.

Given below are specific examples which confirm that biostimulating agent No. 2 is effective 1. Patient P., age,52, suffered from the 2nd stage hypersonic disease, obesity (her weight was 112 kg), and from constipations.

The total cholesterol content in blood was 7.8 mmole/l. She complained of becoming rapidly got tired, her mood was not stable and she was given to crying.

After 45 days of the administration period, an improved state of health an increased tonus, much less crying were reported. Her stool normalized (2 or 3 times a day), her weight decreased to 99 kg (13,4–12%), the cholesterol content decreased to 6.3 mmole/l (15%). The patient reduced the number and amount of hypertensive drugs taken.

2. Patient K., 47 suffered from ischemic heart disease, his weight was 98 kg and he was 176 cm tall. The total cholesterol content in blood was 7.2 mmole/l. He had been suffering from constipations for 8 years, erection had become worse for the last year. His psychoemotional state was depressed .

After the drug intake course of 45 days with intervals of 5 days every 15 days of dry intake. The body weight decreased to 86 kg, stool occurred daily, the total cholesterol content was 5.9 mmole/l. The patient's state of health improved significantly, stenocardia attacks decreased in number, erection improved and depression symptoms decreased considerably.

The agent is used for prophylaxis of atherosclerosis, normalization of the functioning of the sexual glands, reduction of the cholesterol content, prophylaxis of constipations and normalization of functioning of intestine, reduction of excessive body weight; prophylaxis of endemic goiter, weakening of the clinical symptomatology of preclimacteric and climateric, improvements in the immune system characteristics and normalization of the mineral metabolism.

EXAMPLE 2

Biostimulating Agent No. 4

The drug is taken in the form of granules. The dose is a spoonful, 3 or 4 times a day.

The biostimulating agent was tried on 60 volunteers who suffered from urolithasis, pyelitis and inflammation of the urinary bladder. The administration course lasted 90 days.

The clinical tests achieved the following results.

1. Intensification of the antiinflammatory effect by 60–65% as compared with patients who took a pure madder root drug.

2. 72% of patients who took the drug of the present invention showed disappearance of concrements.

3. 94% of patients in the control group (the presence of chronically relapsing formation of concrements for the last 8–11 years when patients took a pure madder drug showed no relapse of formation of concrements for a period of 12 months. Thus biositmulating agent No. 4 is capable of, simultaneously loosening and removing renal calculi, preventing their subsequent formation due to affecting the main pathogenic links of lithogensis and also producing spasmolytic diuretic effect.

EXAMPLE 3

Biostimulating Agent No. 5

The drug is taken in the form of granules of 3–5 gramms, 2 or 3 times a day. The intake course lasted 90 days.

The biostimulating agent was tried on 65 volunteers (41 women and 24 men from 46 to 64 years of age).

Besides, comparative analysis was carried out for the control group of patients (65 men and women) who took a pure birch fungus drug.

The test results obtained were as follows.

1.95% of patients showed greater working capacity, lower fatiguability, reduced pain syndrom. 32% of patients of the control group who took a pure birch fungus drug showed reduced pain syndrom lower fatiguability, greater working capacity as compared with the group of patients who were treated by traditional methods.

2. 90% of patients who suffered from constipations had a fewer number of constipations. The number of patients of the control group who took a pure birch fungus drug and had a fewer number of constipations amounted to 24%.

3. 85% of patients showed an increased amount of T- and B lymphocytes by 15–19%. The patients of the control group who took a pure birch fungus drug (22%) showed increased amount of T-and B lymphocytes by 3–5%.

4. Patients showed improved tolerability of the medicinal treatment, better skin condition, improved observed condition (when gastroscopy was carried out) of the gastro mucosa and duodenum (by 65–70% more pronounced effect than that in the control group of patients).

5. Patients who suffered from malignant diseases showed a pronounced antianemic effect. The patients of the control group showed an effect by 40–43% higher than that in the group of patients who took only a birch fungus drug.

During the drug intake period, none of the patients showed an exacerbation.

Given below are specific clinical examples confirming the fact that biostimulating agent No. 5 is effective.

1. Patients A., 58 suffered from chronic spastic constipations. After taking the drug for a certain period of time her regular stool was restored and she showed no pain and dyspeptic syndromes.

2. Patients B, 65, had multiple parasitic invasion: ascarides, enterobiosis, lyombliosis.

The preparation of the present invention was prescribed for preparation for a complex antiparasitic therapy form the moment of prescription, patients showed normalization of the liver size, disapperance of the pain syndrom and pathological abdominal symptoms and normalization of the stool.

3. Patients B, 51, had chronic surface gastritis with increased acid secretion. The patient had an exacerbation stage and dyskinesia of bileferous tracts, and lambliasis.

The effect: the stool became normal (earlier constipations occured up to 3 or 4 days), the tongue become clean the liver rapidly got smaller in size and the morphological pattern of the stomach mucuous membrane improved.

4. Patient 6, 54 had stomach tumor. He took the drug of the present invention during the chemiotherapy course.

The positive effects were ascertained: patients showed no diarrhea and improved properties of peripheral blood (more rapid restoration of these properties).

EXAMPLE 4

Biostimulating Agent No. 3

The drug is taken in the form of granules. The drug with a weight of 3–5 g is taken 2 or 3 times a day.

The agent of the present invention was tried on 80 volunteers (48 woman and 32 men aged from 25 to 63) and the intake course lasted 90 days.

Besides, a comperative analysis was carried out with the control group of patients (80 men and women) who took a pure oats drug.

The test results obtained were as follows.

1. 82% of patients who suffered from constipations and diarrehea and 21% of the patients of the control group who took a pure oats drug showed normalization of stool.

2. 93% of patients and 45% of the patients of the control group who took a pure oats drug showed normalization of the liver function test. 75% of patients and 33% of the patients of the control group who took a pure oats drug showed improved peristalsis of the gallbladder.

3. 90% of patients and 26% of the patients of the control group who took a pure oats drug showed a reduced pain syndrom.

4. 85% of patients and 36% of the patients of the control group showed a reduced cholesterol content by 29% and 14% respectively 5. 89% of patients and 34% of the patients in the control group showed a reduced triglyceride content in blood by 30% and 16%, respectively.

6. 58% of patients and 11% of the patients of the control group showed normalized blood coagulation.

During the drug intake period, patients showed no case of exacerbation.

Given below are specific clinical examples which confirm the fact that biostimulating agent No. 3 is effective.

1. Patient G., 48, suffered from chronic cholecystitis and dyskinesia of the biliferous tracts. After the drug intake course, a cupping of a pain syndrom, normalization of stool and improved appetite were observed.

2. Patient S. 60, suffered from thrombophlebitis of the lower extremities and trophic ulcers. After the drug intake course a reduced pain syndrome and adhesion of trophic ulcers were observed.

3. Patient B., 55, suffered from 3rd stage obesity, stenocardia, and atherosclerosis. After the drug intake course, patients showed a reduced cholesterol content in blood by 26% and reduced body weight by 7 kg.

4, Patient R., 29, suffered from chronic hepatitis B. After the drug intake course patients showed normalization of the liver function test and blood bilirubin.

Biostimulatinq agent No. 3 is effective in case of disorders in the function of the liver, the gallbladder, the pancreas, and in case of gastrities, gastrodoudenites, enterocities or the like.

EXAMPLE 5

Biostimulating Agent No.1

The agent was taken in the form of granules having a weight of 3–5 g, 2 or 3 times a day. The drug intake course lasted 30 days. The biostimulating agent was tried on 350 volunteers (195 women and 155 men aged from 27 to 72). Besides, a comparative analysis was carried out with the control group of patients (350 women and men) who took only a bran drug.

The test results were as follows:

1. 98% of patients and 15% of patients of the control group who took only a bran drug showed a reduced pain syndrome, 49% of patients and 7% of the patients, of the control group who took only a bran drug showed greater working capacity.

2. 73% of patients and 24% of the patients of the control group who took only a bran drug showed an antianemic effect.

3. 98% of patients who suffered from constipations and diarrhea and 32% of the patients of the control group who took only bran drug, had no constipations.

4. 66% of patients and 4% of the patients of the control group who took only a bran drug showed no depressive state caused by stress.

5. 85% of patients and 34% of the patients of the control group who took only a bran drug showed elimination of the process of acute and consequences of chronic poisonings.

6. 84% of patients and 15% of the patients of the control group who took only a bran drug showed an improved state of the stomach gastric mucosa and duodenum as evidenced by a gastroscopy test.

During the drug intake period, patients had not a single case of exacerbation.

Thus, clinical tests confirmed the fact that the biostimulating agent of the present invention normalized the mineral balance in the body. This balance is based on resistance of the body to diseases of different ethiology. The agent of the present invention makes it possible to produce a higher therapeutic effect as compared with the traditional agents.

The agent of the present invention is effective in particular in case of diseases of the intestinal tract, for the propylaxis of atherosclerosis, in case of diseases of kidneys urinary bladder, urollthiasis. The agent produces a tonic effect, reduces a pain syndrom, promotes an immune-modulating effect.

What is claimed is:

1. A biostimulating agent comprising natural minerals having ion-exchange and sorption properties and a vegetable stock, said natural minerals selected from the group consisting of clinoptilotite-heulandite zeolite containing not less than 92 wt. % of clinoptilolite, montmorillonite clay comprising not less than 92 wt. % of montmorillonite and mixtures thereof, said vegetable stock, comprising cereals selected from the group consisting of wheat bran and rye bran, waste thereof, higher herbaceous plants, sea algae, and higher fungi, wherein the ratio of the components is as follows (wt. %):

| | |
|---|---|
| natural minerals | 33–62 |
| vegetable stock | 34–61 |
| water | the balance. |

2. The biostimulating agent according to claim 1, wherein said montmorillonite clay comprises not less than 92 wt % of montmorillonite and Japanese laminaria (Laminaria japonica Aresh), the ratio of the components being as follows (wt %):

| | |
|---|---|
| montmorillonite | 49–51 |
| Japanese laminaria | 46–44 calculated [by] dry matter |
| water | [to] the balance. |

3. A biostimulating agent according to claim 1, wherein said clinoptilolite-heulandite zeolite comprises not less than 92 wt % of clinoptilolite, comprising not less than 92 wt % montmorillonite and oats, the ratio of the components being as follows (wt %):

| | |
|---|---|
| zeolite | 29–31 |
| montmorillonite | 29–31 |
| oats | 34–36 (calculated [by] dry matter) |
| water | the balance. |

4. The biostimulating agent according to claim 1, wherein said clinoptilolite-heulandite zeolite comprises not less than 92 wt % clinoptilolite montmorillonite clay comprising not less than 92 wt % of montmorillonite, madder (*Rubia tinctorum*) root, the ratio of the components being as follows (wt %):

| | |
|---|---|
| zeolite | 14–16 |
| montmorillonite | [21–19] 19–21 |
| madder | 59–61 (calculated [by] dry matter) |
| water | [to] the balance. |

5. The biostimulating agent according to claim 1, wherein said clinoptilolite, montmorillonite clay comprises not less than 92 wt % of montmorillonite, birch fungus Ionotus obliquus), the ratio of the components being as follows (wt %):

| | |
|---|---|
| zeolite | 14–16 |
| montmorillonite | [21–19] 19–21 |
| birch fungus | 59–61 |
| water | [to] the balance. |

6. The biostimulating agent according to claim 1, characterized in that it is made in the form of powder, tablets, granules, and lozenges.

7. The biostimulating agent according to claim 2, characterized in that it is made in the form of powder, tablets, granules and lozenges.

8. The biostimulating agent according to claim 3, characterized in that it is made in the form of powder, tablets, granules and lozenges.

9. The biostimulating agent according to claim 4, characterized in that it is made in the form of powder, tablets, granules and lozenges.

10. The biostimulating agent according to claim 5, characterized in that it is made in the form of powder, tablets, granules and lozenges.

11. A method for the treatment of bowel disease comprising administering an effective dose of a therapeutic agent as recited in claim 1.

12. The biostimulating agent according to claim 1 wherein the ratio of components is as follows (wt. %):

| | |
|---|---|
| zeolite | 49–51 |
| wheat bran | 24–26 |
| rye bran | 19–21 |
| water | balance. |

13. The biostimulating agent according to claim 12 wherein said biostimulating agent is made in the form of powder, tablets, granules or lozenges.

* * * * *